United States Patent
Nauta

[11] 3,980,650
[45] Sept. 14, 1976

[54] 4-AMINO-PYRIMIDINE DERIVATIVES

[75] Inventor: Wijbe Thomas Nauta, Nieuw Loosdrecht, Netherlands

[73] Assignee: N.V. Koninklijke Pharmaceutische Fabrieken v/h Brocades-Stheeman en Pharmacia, Netherlands

[22] Filed: May 20, 1974

[21] Appl. No.: 471,590

Related U.S. Application Data

[63] Continuation of Ser. No. 250,614, May 5, 1972, abandoned.

[52] U.S. Cl. ............... 260/256.4 Q; 260/239 B; 260/247.5 DP; 260/268 H; 260/294.9; 260/326.62; 424/251
[51] Int. Cl.² .............................. C07D 239/94
[58] Field of Search ............ 260/256.4 Q, 247.5 DP

[56] References Cited
UNITED STATES PATENTS

| | | | |
|---|---|---|---|
| 3,322,759 | 5/1967 | Carney et al. | 260/256.4 Q |
| 3,511,836 | 5/1970 | Hess | 260/256.4 Q |
| 3,574,212 | 4/1971 | Hess | 260/256.4 Q |
| 3,635,979 | 1/1972 | Hess | 260/256.4 Q |
| 3,669,968 | 6/1972 | Hess | 260/256.4 Q |
| 3,757,017 | 9/1973 | Mathieu | 260/256.4 Q |
| 3,772,295 | 11/1973 | Robba et al. | 260/256.4 Q |
| 3,819,628 | 6/1974 | Simpson | 260/256.4 Q |

FOREIGN PATENTS OR APPLICATIONS

| | | | |
|---|---|---|---|
| 6,608,538 | 12/1967 | Netherlands | 260/256.4 Q |

OTHER PUBLICATIONS

Burger, "Medicinal Chemistry," 1963, p. 42.
Taylor et al., J. Org. Chem., 26, 4967–4974, (1961).
Andrisano et al., Gazz Chim. Ital., 80, 228–233 (1950).

*Primary Examiner*—Richard J. Gallagher
*Assistant Examiner*—David E. Wheeler
*Attorney, Agent, or Firm*—Robert E. Burns; Emmanuel J. Lobato; Bruce L. Adams

[57] ABSTRACT

A process is described for the preparation of pyrimidine derivatives having therapeutic properties. They have the general formula:

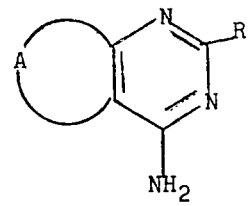

I wherein A represents an alkylene or alkenylene grouping which together with the carbon atoms of the pyrimidine nucleus to which it is attached forms a homocyclic ring containing five to seven carbon atoms, which homocyclic ring may carry one or more halogen, lower alkyl and/or lower alkoxy substituents and R represents an amino, lower alkylamino or di(lower-)alkylamino group, or a nitrogen-, oxygen- or sulphur-containing saturated or unsaturated mononuclear heterocyclic group linked to the pyrimidine ring either through a carbon atom or, when the group contains a nitrogen atom, either through the nitrogen atom or a carbon atom and are prepared by reacting a cycloaliphatic(A)oaminonitrile with a nitrile of the formula R-CN where A and R have the above meanings in the presence of a basic alkali metal-containing compound and then reacting the resultant intermediate with water. The compounds have heretofore undiscovered antimicrobial and antihypertensive properties.

6 Claims, No Drawings

4-AMINO-PYRIMIDINE DERIVATIVES

This is a continuation of application Ser. No. 250,614, filed May 5, 1972, now abandoned.

This invention relates to a new process for the preparation of pyrimidine derivatives, to new therapeutically useful pyrimidine derivatives and salts thereof and to pharmaceutical compositions containing them.

The process of the invention is concerned with the preparation of pyrimidine derivatives of the general formula:

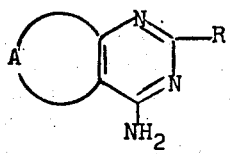

I wherein A represents an alkylene or alkenylene grouping which together with the carbon atoms of the pyrimidine nucleus to which it is attached forms a homocyclic ring containing five, six or seven (preferably six) carbon atoms, which homocyclic ring may carry one or more substituents selected from halogen atoms and lower alkyl and lower alkoxy groups (preferably methoxy), the total number of carbon atoms in the alkyl and/or alkoxy substituents being not more than eight, and R represents an amino, lower alkylamino or di(lower)alkylamino group, or a nitrogen-, oxygen- or sulphur-containing saturated or unsaturated mononuclear heterocyclic group (preferably containing five to seven atoms in the ring) linked to the pyrimidine ring through a carbon atom or, when the group contains a nitrogen atom, either through the nitrogen atom or a carbon atom (e.g., 2-, 3- or 4-pyridyl, pyrrolidinyl, piperidino, morpholino or furyl), said heterocyclic group optionally carrying one or more halogen atoms or lower alkyl or lower alkoxy substituents and/or, when it contains a nitrogen atom not directly linked to the pyrimidyl group, an N-acyl substituent (preferably a lower alkanoyl benzoyl or furoyl group). By the term "lower" as applied herein to alkyl, aklkoxy and alkanoyl groups is meant that the group in question contains at most eight (and preferably at most four) carbon atoms.

According to the invention, the pyrimidine derivatives of general formula I are prepared by reacting a cycloaliphatic o-aminonitrile of the formula:

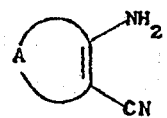

II (wherein A is as hereinbefore defined) with a nitrile of the formula:

R — CN   III (wherein R is as hereinbefore defined) in the presence of a basic alkali metal-containing compound and decomposing the intermediate product of the general formula:

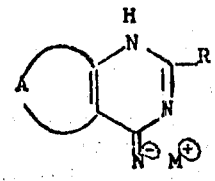

IV (wherein A and R are as hereinbefore defined, and M represents an alkali metal atom) by addition of water. Preferred alkali metl-containing compounds are organo metallic compounds such as phenyl lithium or mesityl lithium. Examples of other alkali metal-containing compounds that may be used are a. complexes of alkyl compounds with amines, such as the complex of butyl lithium with tetramethylethylenediamine, b. hydrides, such as sodium hydride, and c. alkoxides, such as sodium methoxide.

The reaction is preferably carried out at a temperature between —35° and +250°C. preferably 30° – 100°C., in the absence of water under an inert gaseous atmosphere, e.g. nitrogen, in an organic solvent such as a di(lower)alkyl ether (preferably diethyl ether), tetrahydrofuran or benzene. When the alkali metal compound is an alkoxide, alcohols such as ethanol or isopropanol may also be used as a solvent.

The cycloaliphatic o-aminonitriles of formula II are known compounds or they may readily be obtained by methods described in the literatrure, e.g. in "The Chemistry of Cyclic Enaminonitriles and o-Aminonitriles" by E. C. Taylor and A. McKillop*. E. C. Taylor and A. L. Borror, J. Org. Chem. 26, 4967 – 74 (1961), investigated the reaction of 2-aminobenzonitrile with a number of aromatic and aliphatic nitriles. The reactions were generally performed in methanolic ammonia. Severe conditions were necessary (e.g. heating in a sealed tube for 20 hours at 200°C) to obtain their desired compounds. One reaction in methanol in the presence of sodium methoxide is reported but heating in a sealed tube was necessary and no reaction occured in refluxing methanol. In the process of the present invention good results are obtained under mild conditions.

*Advances in Organic Chemistry, Vol. 7, 1970 Interscience Publications

A great number of compounds of formula III are already known. New compounds of this formula wherein the cyano group is linked to a carbon atom of a heterocyclic group may generally be obtained by reaction of a compound RH (wherein R is a heterocyclic group as hereinabove defined) with dimethyl formamide in the presence of phosphorus oxychloride or phosgene (Vilsmeier - Haack reaction) and reacting of the resulting aldehyde with hydroxylamine, sodium formate and formic acid. New compounds of formula III wherein the cyano group is linked to a nitrogen atom may be prepared by addition of cyanogen bromide to a solution of the secondary amine in an organic solvent.

Important compounds of general formula I which may be obtained by the process of the invention are those in which A together with the carbon atoms to which it is attached forms a benzene ring, e.g. the 4-aminoquinazolines of the general formula:

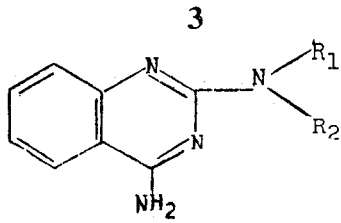

(wherein $R_1$ and $R_2$ are the same or different and each represents a hydrogen atom or a lower alkyl group or together with the nitrogen atom to which they are attached represent a saturated or unsaturated, optionally substituted mononuclear heterocyclic group, preferably containing five to seven atoms in the ring, which may contain a further hetero atom, and wherein the homocyclic ring of the quinazoline nucleus may carry, for example, one or more substituents selected from halogen atoms and lower alkyl and lower alkoxy groups) which are known, pharmacologically active compounds. Compounds of this type are described in, for example, U.S. Pat. Ser. No. 3,511,836. In that specification the compounds are stated to have therapeutic utility as hypotensive agents. According to this patent, synthesis of compounds of formula V is preferably carried out in a multi-step process in which initially a 2,4-dichloro-quinazoline is formed by reaction of an anthranilic acid, or amide, nitrile or ester thereof, with sodium or potassium cyanate, cyclization of the uredio compound obtained to a 2,4-dihydroxy-quinazoline and chlorination thereof using a mixture of phosphorus pentachloride and phosphorus oxychloride. This process is illustrated for one compound by the following reaction scheme:

wherein $R_3$ represents a saturated or unsaturated mononuclear heterocyclic group attached to the quinazoline nucleus through carbon (preferably containing five to seven atoms in the ring), which may carry one or more halogen atoms or lower alkyl or lower alkoxy groups and/or, when it contains a nitrogen atom, an N-acyl substituent (preferably a lower alkanoyl, benzoyl or furoyl group), and the symbols $R_4 - R_7$ represent hydrogen atoms, halogen atoms or lower alkyl or lower alkoxy groups, the total number of carbon atoms in alkyl or alkoxy groups, when present, being not more than eight, and their acid addition and quaternary ammonium salts. Said compounds of general formula VI are therapeutically useful.

The compounds of general formula VI except for the compound in which $R_3$ represents a 2-furyl group and $R_4 - R_7$ are hydrogen atoms, i.e 4-amino-2-(2-furyl)-quinazoline*, are new and are another feature of the invention. Preferred compounds of general formula VI are those in which $R_5$ and $R_6$ are the same or different and each represents a hydrogen or halogen atom, or a lower alkyl or lower alkoxy group, and $R_4$ and $R_7$ represent hydrogen atoms.

*Andrisano, R. & Modena, G.; Gazz. Chim. Ital. 80 pgs. 228–233

The compounds of formula VI are active against pleuropneumonia-like organisms such as *Mycoplasma gallisepticum*, the causative agent of chronic respiratory disease in poultry. The most pronounced activity is found in those compounds in which $R_3$ represents a 2-pyridyl group and especially in 4-amino-6-chloro-2-(2-pyridyl)quinazoline and its salts. The compounds of formula VI are also active against other gram negative

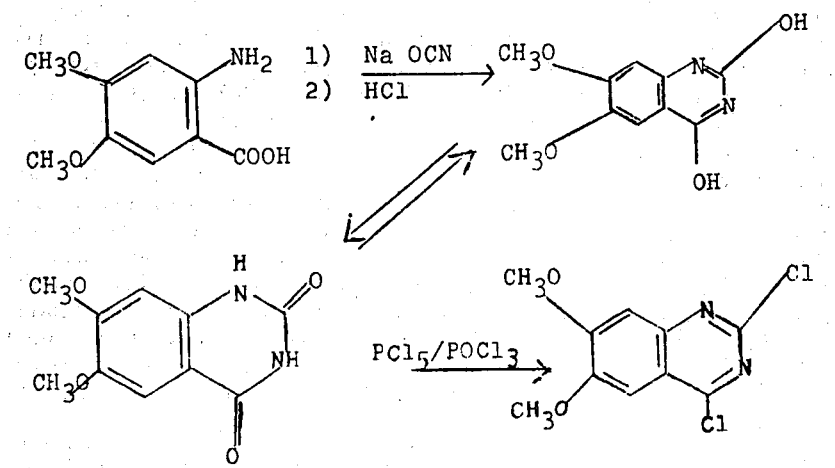

The 2,4-dichloroquinazoline is then reacted with the appropriate amino compounds to obtain the desired end product. By the process of the present invention compounds of the same type may be obtained in a much simpler and more direct way.

The new process may also be used for the preparation of 4-aminoquinazoline derivatives of the general formula:

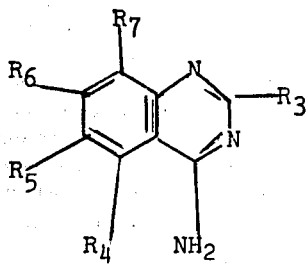

bacteria, such as *Pasteurella multocida*.

The quinazoline derivatives of formula VI also exert an anti-hypertensive activity. Prefered compounds in this respect are those in which $R_3$ represents a pyridyl or furyl group, especially 4-amino-2-(4-pyridyl)-quinazoline and 4-amino-6,7-dimethoxy-2-(2-furyl)-quinazoline and their salts, which have proved to be very active in rats that were made hypertensive by the technique of H. Goldblatt et al., Exp. Med. 59, 340 (1934). They may be administered alone or in conjunction with other therapeutically acting compounds effective for controlling hypertension.

For use as therapeutics, the compounds of general formula VI may be used as such or as non-toxic acid addition or quaternary ammonium salts, i.e., salts which are not harmful to the animal organism when used in therapeutic doses. Such acid addition salts may be derived from inorganic acids, such as the hydrohalic acids (e.g. hydrochloric and hydrobromic acid) and sulphuric acid, and organic acids such as oxalic, maleic, tartaric, citric, acetic, lactic, succinic, fumaric and pamoic acid. The bases or non-toxic acid addition or quaternary ammonium salts thereof may be administered orally or parenterally in a pharmacologically acceptable carrier according to accepted pharmaceutical practice.

The dosage and method of administration will depend on the species and the disease treated. When used for combatting chronic respiratory disease in poultry the compounds are suitably administered with the animal fodder so as to give daily intakes of from 25 to 100 mg/kg animal body weight. For this purpose feed compositions containing 25 to 250 g of the active substance per ton are suitably used. It is also possible to prevent the disease by injecting the eggs with ca. 0.5 ml of an aqueous solution of 1–5 g/l of the active substance. The dosages to be applied in the treatment of hypertension will depend on the mammalian species treated. Examples of suitable oral daily doses are 25 to 150 mg. for adult humans and dogs, and 1 to 5 g. for horses.

Acid addition and quaternary ammonium salts of the pyrimidine derivatives of formula VI may be prepared by methods known per se. For example, the base may be treated with the equivalent amount of the acid in an inert solvent to obtain the corresponding acid addition salt, or the base may be treated with the equivalent amount of an appropriate alkyl halide or dialkyl sulphate in a solvent having a high dielectric constant, for example acetonitrile, to obtain the quaternary ammonium salts.

The following Examples illustrate the preparation of compounds of the invention.

EXAMPLE I

Under a nitrogen atmosphere 4.7 g. (0.03 mol) of bromobenzene dissolved in 35 ml. of anhydrous diethyl ether, are added to 0.42 g. (0.06 mol) of lithium. To the solution obtained, a solution of 0.03 mol o-aminobenzonitrile in 15 ml. of anhydrous diethyl ether is added dropwise at room temperature. After about 10 minutes, a solution of 0.03 mol diethylcyanamide in 10 ml. of anhydrous diethyl ether is added dropwise. The reaction mixture is then refluxed under the nitrogen atmosphere for 4 hours. The next day the mixture is decomposed by addition of water. The ethereal layer is separated off, washed with water, dried over sodium sulphate and concentrated by evaporation of solvent. Some petroleum ether (boiling range 28°–40°C.) is added to the residue, the solid is filtered off and crystallized from a mixture of methanol and water. 4-Amino-2-diethylaminoquinazoline, m.p. 125°–128°C., is obtained.

The base is converted into the monohydrochloride by dissolution in diethyl ether and addition of an equivalent amount of hydrogen chloride, dissolved in diethyl ether. M.P. 237° – 239°C.

EXAMPLE II

Using the procedure described in Example I but substituting an equivalent amount of 1-pyrrolidine carbonitrile for the diethylcyanamide, 4-amino-2-(1-pyrrolidyl)quinazoline, m.p. 215°–216°C., is obtained.

EXAMPLE III

Under a nitrogen atmosphere 0.7 g. (0.10 g. at.) of lithium and 7.85 g. (0.05 mol) of bromobenzene are dissolved in 60 ml. of anhydrous diethyl ether. Over the course of about 20 minutes this solution is added to a solution of 5.9 g. of o-aminobenzonitrile in 60 ml. of anhydrous diethyl ether. After 10 minutes, 3.5 g. of dimethylcyanamide, dissolved in 20 ml. of anhydrous diethyl ether, are added and the reaction mixture is refluxed under the nitrogen atmosphere for 6 hours. The next day the mixture is decomposed by addition of water and the precipitate is filtered off. The product is crystallized from a mixture of ethanol and petroleum ether (boiling range 28°–40°C.). 6 g. of 4-amino-2-dimethylaminoquinazoline, m.p. 141°–142°C., are obtained.

The base is converted into the monohydrochloride by dissolution in ethanol and addition of an equivalent amount of hydrogen chloride dissolved in diethyl ether. The hydrochloride is crystallized from a mixture of methanol and diethyl ether. M.P. above 300°C.

EXAMPLE IV

Using the procedure described in Example III but substituting an equivalent amount of 6-aminoveratronitrile dissolved in tetrahydrofuran for the o-aminobenzonitrile dissolved in diethyl ether, 4-amino-2-dimethylamino-6,7-dimethoxyquinazoline, m.p. 223°–224°C., is obtained.

EXAMPLE V

Using the procedure described in Example I but substituting an equivalent amount of 6-aminoveratronitrile dissolved in tetrahydrofuran for the o-aminobenzonitrile dissolved in diethyl ether, 4-amino-2-diethylamino-6,7-dimethoxyquinazoline, m.p. 167°–169°C., is obtained. The monohydrochloride after crystallization from isopropanol melts at 250°C. (decomp.)

EXAMPLE VI

To 3.6 g. of 6-aminoveratronitrile, dissolved in 75 ml. of anhydrous benzene, a solution of phenyl lithium (prepared from 0.35 g. of lithium and 3.9 g. of bromobenzene) in 60 ml. of anhydrous diethyl ether is added under a nitrogen atmosphere. After 45 minutes 4.4 g. of 1-cyano-4-(2-furoyl)piperazine in 50 ml. of anhydrous benzene are added. The ether and part of the benzene are distilled off and 100 ml. of tetrahydrofuran are added. The mixture is refluxed under the nitrogen atmosphere for 20 hours and then decomposed with water. The liquid is distilled off and 75 ml. of water are added to the residue. The mixture is extracted with chloroform and the extract is concentrated by evaporation of the solvent. 1-(4-Amino-6,7-dimethoxy-2-quinazolinyl)4-(2-furoyl)piperazine is obtained. The product after crystallization from a mixture of ethanol and water melts at 258°–260°C.

The base is dissolved in 200 ml. of warm ethanol and a solution of hydrogen chloride in diethyl ether is added. On cooling the monohydrochloride crystallizes. The salt after crystallization from methanol melts at 276°–280°C. (decomp.) Molecular weight determined by titration: 422 (calculated 422.5).

The 1-cyano-4-(2-furoyl)piperazine, used as a starting material, is prepared as follows.

To a solution of 21.5 g. (0.25 mol) of piperazine in a mixture of 960 ml. of acidified water (pH = 4.5) and 1200 ml. of acetone, 32.5 g. (0.25 mol) of furoyl chloride are added dropwise while the pH is maintained at 4.5 by dropwise addition of a sodium hydroxide solution. The mixture is made alkaline, and extracted several times with chloroform. The chloroform is distilled off and the concentrated extract is distilled in vacuo. 18.3 g. of the N-(2-furoyl)piperazine thus obtained in 50 ml. of diethyl ether are added to an equivalent amount of cyanogen bromide in a mixture of 60 ml. of water and 60 ml. of diethyl ether. The mixture is stirred overnight at room temperature and then subjected to continuous extraction with benzene. The extract is dried over sodium sulphate and the solvent is distilled off. According to the NMR and IR spectra the residue consists of 1-cyano-4-(2-furoyl)piperazine, m.p. 63°–65°C.

EXAMPLE VII

Using the procedure described in Example I but substituting the diethylcyanamide by an equivalent amount of 2-pyridine carbonitrile, 4-amino-2-(2-pyridyl)-quinazoline, m.p. 163°–165°C., is obtained. The monohydrochloride after crystallization from a mixture of isopropanol and ethanol melts at 255°C.

In an analogous way there are obtained 4-amino-2-(3-pyridyl)quinazoline dihydrochloride, m.p. 232°–235°C. (decomp.), and 4-amino-2(4-pyridyl)-quinazoline dihydrochloride, m.p. 280°C. (decomp.)

EXAMPLE VIII

Using the procedure described in Example III, but substituting an equivalent amount of 2-amino-5-chlorobenzonitrile for the o-aminobenzonitrile and an equivalent amount of 2-pyridine carbonitrile for the dimethylcyanamide, 4-amino-6-chloro-2-(2-pyridyl)quinazoline, m.p. 265°–268°C., is obtained.

EXAMPLE IX 5.4 g. (0.05 mol) of o-aminobenzonitrile, 4.7 g. (0.05 mol) of 2-furonitrile and 5.4 g. (0.1 mol) of sodium methoxide in 150 ml. of isopropanol are refluxed for 48 hours under a nitrogen atmosphere. The reaction mixture is then decomposed with water and the isopropanol is distilled off. 80 ml. of diethyl ether and 80 ml. of water are added and the precipitate is filtered off. The ethereal layer is separated and the ether is distilled off. The residue is identical to the solid already filtered off. The product is crystallized from a mixture of ethanol and petroleum ether (boiling range 40°–60°C.) to give 4-amino2-(2-furyl)quinazoline, m.p. 219°–221°C. The base is converted into the monohydrochloride, and the salt after crystallization from ethanol melts above 300°C.

EXAMPLE X 8.9 g. (0.05 mol) of 6-aminoveratronitrile, 5.2 g. (0.05 mol) of 2-pyridine carbonitrile and 5.4 g. (0.1 mol) of sodium methoxide in 250 ml. of isopropanol are refluxed for 48 hours under a nitrogen atmosphere. The reaction mixture is then decomposed with water and the isopropanol is distilled off. 80 ml. of diethyl ether and 80 ml. of water are added and the layers are separated. The water is distilled off from the aqueous layer and the residue is dissolved in 100 ml. of chloroform. The solution is filtered and the chloroform is distilled off. The residue is crystallized from toluene to give 4-amino-6,7-dimethoxy-2-(2-pyridyl)quinazoline, m.p. 248° – 251°C. The base is converted into the monohydrochloride, and the salt after crystallization from a mixture of water and isopropanol, melts above 310°C.

Using the same procedure but substituting an equivalent amount of the appropriate nitrile for the 2-pyridine carbonitrile, the following compounds are obtained:
4-amino-6,7-dimethoxy-2-(2-furyl)quinazoline hydrochloride, m.p. 285° – 287°C, 4-amino-6,7-dimethoxy-2-morpholinoquinazoline,
4-amino-6,7-dimethoxy-2-piperazinoquinazoline,
4-amino-6,7-dimethoxy-2-(2-tetrahydrofuryl)quinazoline,
4-amino-6,7-dimethoxy-2-piperidinoquinazoline,
4-amino-6,7-dimethoxy-2-hexahydroazepinoquinazoline,
4-amino-6,7-dimethoxy-2-pyrrolidinoquinazoline,
4-amino-6,7-dimethoxy-2-(4-pyridyl)quinazoline,
4-amino-6,7-dimethoxy-2-(3-pyridyl)quinazoline,
4-amino-6,7-dimethoxy-2-(2,6-dimethylmorpholino)-quinazoline.

EXAMPLE XI

Using the procedure of Example I but substituting an equivalent amount of 1-methyl-2-pyrrole carbonitrile for the diethylcyanamide, 4-amino-2-(1-methyl-2-pyrrolyl)quinazoline monohydrochloride is obtained. The compound after crystallization from a mixture of isopropanol and ethanol melts at 278° – 280°C.

The invention includes within its scope pharmaceutical preparations comprising, as at least one of the active ingredients, at least one of the new-therapeutically active compounds of general formula VI, or non-toxic acid addition or quaternary ammonium salt thereof, in association with a pharmaceutically-acceptable carrier. The preparations may take any of the forms customarily employed for administration of therapeutically active substances, but the preferred types are those suitable for oral administration and especially tablets, including sustained release tablets, and capsules including the substance. The tablets may be formulated in the usual manner with one or more pharmaceutically-acceptable diluents or excipients, for example lactose or starch, and include materials of a lubricating nature, for example calcium or magnesium stearate. Capsules made of absorbable materials, such as gelatin, may contain the active substance alone or in admixture with a solid or liquid diluent. Liquid preparations are little used for the present therapeutic indication, but if required such preparation may be made in the form of suspensions, emulsion, syrups or elixirs of the active substance in water or other liquid medium commonly used for making orally acceptable pharmaceutical formulations, such as liquid paraffin, or a syrup or elixir base. The active substance may also be made up in a form suitable for parenteral administration, i.e. as a suspension or emulsion in sterile water or an organic liquid usually employed for injectable preparations, for example a vegetable oil such as olive oil, or a sterile solution in water or an organic solvent.

The following Example illustrates pharmaceutical compositions according to the invention.

EXAMPLE XII 50 g. of 4-amino-2-(4-pyridyl)quinazoline dihydrochloride (sieved through a 40 mesh sieve), 50 g. of Avicol PH 101 (microcrystalline cellulose), and 1 mg. of Aerosil (highly purified silicon dioxide) are mixed together and soft gelatin capsules are filled each with 101 mg. of the mixture so that each capsule contains 50 mg. of active substance.

I claim:

1. 4-Aminoquinazolines of the formula VI:

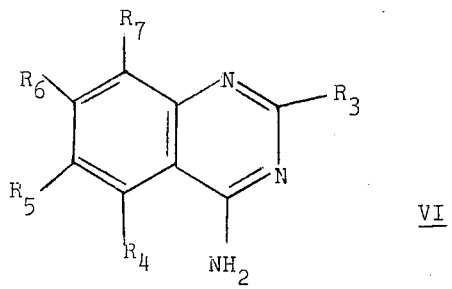

VI wherein:

$R_3$ represents a saturated or unsaturated heterocyclic ring of 5 to 7 ring atoms selected from the group consisting of pyridyl, piperidyl, piperazinyl, morpholinyl, pyrrolyl and azepinyl, said ring being unsubstituted or substituted by one lower alkyl, $R_3$ being attached to the quinazoline nucleus through a ring carbon; and $R_5$ and $R_6$ are the same or different and each represents hydrogen, halogen, lower alkyl or lower alkoxy group and $R_4$ and $R_7$ represent hydrogen, the total number of carbon atoms in said alkyl or alkoxy being not more than four; and the pharmaceutically acceptable acid addition and quaternary ammonium salts thereof.

2. 4-Aminoquinazolines according to claim 1 in which $R_3$ represents a pyridyl moiety.

3. The 4-Aminoquinazoline according to claim 2 in which $R_3$ represents 2-pyridyl.

4. The compound according to claim 3, 4-amino-6-chloro-2-(2-pyridyl)quinazoline and its pharmaceutically acceptable acid addition and quaternary ammonium salts.

5. The 4-Aminoquinazoline according to claim 2 in which $R_3$ represents 4-pyridyl.

6. The compound according to claim 5, 4-amino-2-(4-pyridyl)quinazoline and its pharmaceutically acceptable acid addition and quaternary ammonium salts.

* * * * *